United States Patent
Liberti et al.

(10) Patent No.: US 7,201,311 B2
(45) Date of Patent: Apr. 10, 2007

(54) MESSAGE MAPPING TECHNIQUE

(75) Inventors: Lawrence E. Liberti, Holland, PA (US); Geraldine E. Liberti, Holland, PA (US); Johanna M. Harrison, Holland, PA (US); Sarah Conaway, Horsham, PA (US); John E. Knapp, Yardley, PA (US)

(73) Assignee: Thomson Scientific Inc., Philadelphia, PA (US)

( * ) Notice: Subject to any disclaimer, the term of this patent is extended or adjusted under 35 U.S.C. 154(b) by 61 days.

(21) Appl. No.: 10/956,563

(22) Filed: Oct. 1, 2004

(65) Prior Publication Data

US 2005/0109830 A1 May 26, 2005

Related U.S. Application Data

(60) Provisional application No. 60/507,751, filed on Oct. 1, 2003.

(51) Int. Cl.
*G06F 7/00* (2006.01)

(52) U.S. Cl. .................................................. 235/376
(58) Field of Classification Search ............... 235/376, 235/380, 436
See application file for complete search history.

(56) References Cited

U.S. PATENT DOCUMENTS 5,855,015 A * 12/1998 Shoham ......................... 707/5
6,868,525 B1 * 3/2005 Szabo ......................... 715/738

* cited by examiner

*Primary Examiner*—Daniel Stcyr
(74) *Attorney, Agent, or Firm*—Synnestvedt & Lechner LLP

(57) ABSTRACT

A time savings information management guide that can direct readers to key resources is disclosed. The processes that readers use to identify resources of interest are integrated into a formal reproducible process for large-scale application. The message mapping technique is a process by which the key ideas (messages) described in information resources, including but not limited to books, articles, abstracts, monographs, advertisements, and scientific posters, are identified, categorized, and quantitatively scored for relevance from the point of view of the reader (i.e., consumer, a doctor, researcher, etc).

3 Claims, 5 Drawing Sheets

|  | Not addressed/ No (0) | Not completely described (1) | Clearly described/ Yes (2) |
|---|---|---|---|
| A. Clinical Study Checklist |  |  |  |
| 1. Purpose | • | • | • |
| 2. Disease defined/Question under study | • | • | • |
| 3. Research design | • | • | • |
| 4. Description of treatment protocol | • | • | • |
| 5. Dosage form/route | • | • | • |
| 6. Treatment(s) (placebo, concurrent treatment) | • | • | • |
| 7. Results of study | • | • | • |
| 8. P values | • | • | • |
| 9. Side effects or adverse events | • | • | • |
| 10. Conclusions | • | • | • |
| 11. Study funding identification and relationship to study | • | • | • |
| 12. Unit of observation and variables defined | • | • | • |
| 13. Population characteristics | • | • | • |
| 14. Duration of treatment | • | • | • |
| 15. Study setting | • | • | • |
| 16. Inclusion/exclusion criteria | • | • | • |
| 17. Informed consent | • | • | • |
| 18. Blinding (N/A or open, single, double) | • | • | • |
| 19. Data collection/measures | • | • | • |
| 20. Statistical comparisons | • | • | • |
| 21. Data collection period | • | • | • |
| 22. Participants not meeting inclusion criteria | • | • | • |
| 23. Drop-outs, withdrawals, and lost to follow-up | • | • | • |
| 24. Discussion of analyses | • | • | • |
| 25. Results in context of existing knowledge | • | • | • |
| 26. Generalizability of results | • | • | • |
| 27. Limitations of study | • | • | • |

Total:_____ /Total possible: 54 = _____% (Source Score)

Figure 2

MESSAGE MAPPING TECHNIQUE

BACKGROUND OF THE INVENTION

1. Field of the Invention

This invention relates to the field of the automated searching and indexing of published information.

2. Description of the Related Art

In today's world, information is available everywhere. Historically, periods of time involving rapid and/or significant advancements in a particular area are typically dubbed with a moniker that describes the advancement. Past examples include the "industrial revolution" and the "space age". Today, people describe the current era as the "information age" because never before in the history of mankind has there been more information more easily available to more people.

With this amazing and wonderful access to information comes a significant problem: how to keep track of all of the information available and how to focus in on only the information of interest. In fields such as engineering and medicine, keeping apprised of the latest literature is mandatory for success, yet "information overload" can severely limit the ability of one to do so.

Studies have shown that clinicians generally have only approximately 3–4 hours per week to digest key information. Consequently clinicians cannot review all published information sources but must limit their reading to key items. Checklists have been developed to help quantify the process of assessing scientific information, however, while such checklists are helpful, they still have been hampered by important limitations. These include a lack of applicability to a broad range of resource types, methods that are time-consuming and not optimized based on actual user input, cumbersome definitions and interpretive techniques, and they provide results that do not reflect the actual findings of practicing clinicians.

Accordingly, it would be desirable to have an automated system that ranks scientific information in a way that reflects the selection and reading processes of the reader.

SUMMARY OF THE INVENTION

The present invention provides a time savings information management guide that can direct readers to key resources. In accordance with the present invention, the processes that readers use to identify resources of interest are integrated into a formal reproducible process for large-scale application. The message mapping technique of the present invention is a process by which the key ideas (messages) described in information resources, including but not limited to books, articles, abstracts, monographs, advertisements, and scientific posters, are identified, categorized, and quantitatively scored for relevance from the point of view of the reader (i.e., consumer, a doctor, researcher, etc).

BRIEF DESCRIPTION OF THE DRAWINGS

FIG. 2 illustrates an example of a checklist used to assess the technical merits of an information resource (a clinical article in this example) in accordance with the present invention;

DESCRIPTION OF THE PREFERRED EMBODIMENT

In its most basic form, the present invention comprises a first process that identifies the relevant resources to be evaluated; the use of a checklist to rate the resource strength and identify a "source score" for the relevant resources; and then a second process to identify and score the message strength of each of the relevant resources.

Figure 1:
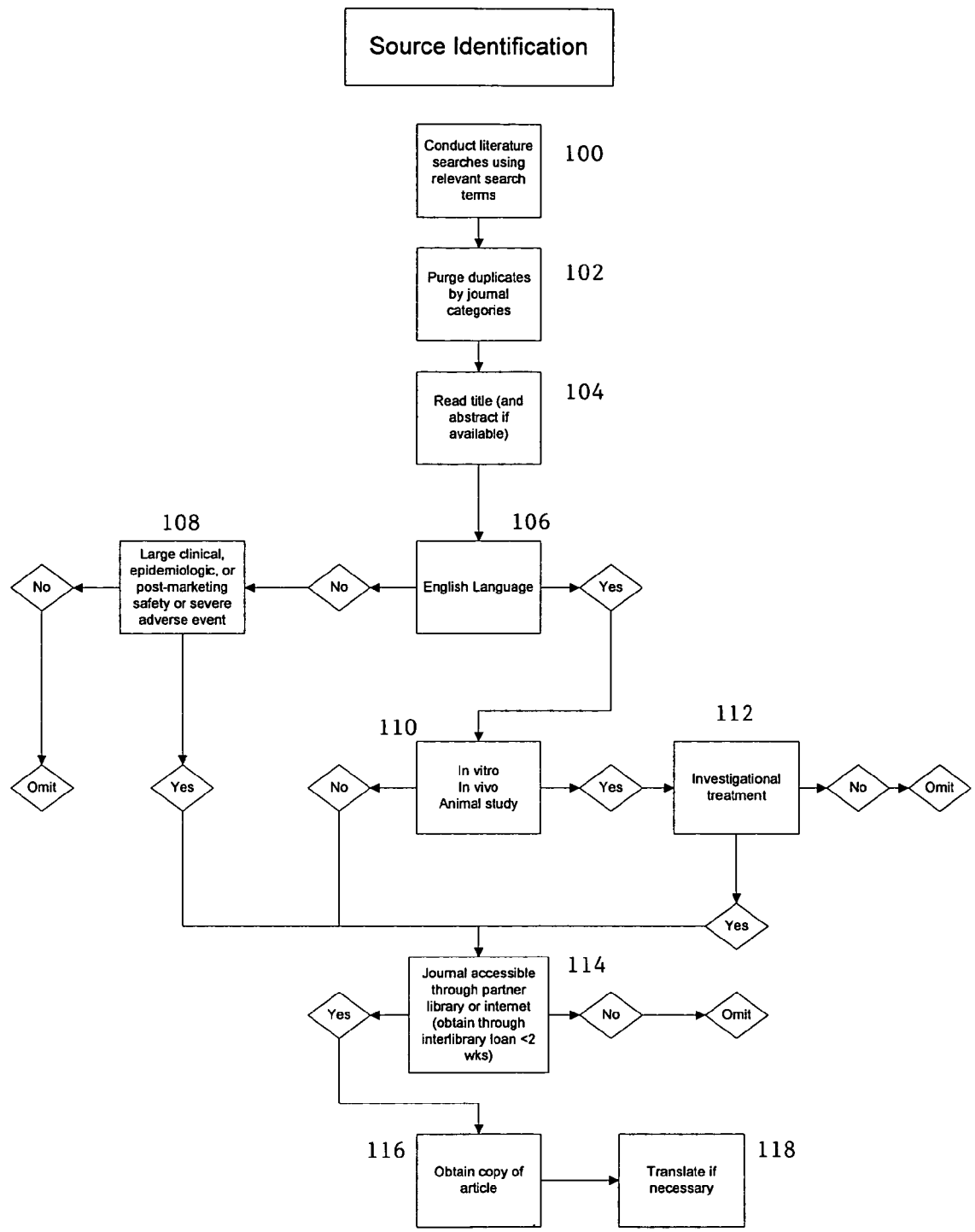
FIG. 1 illustrates a flowchart illustrating the steps performed in a "Source Identification Process" in accordance with the present invention.

FIG. 1 is a flowchart illustrating the steps performed in the first process (the "Source Identification Process"). This provides a standardized technique to identify key information resources and identifies the information resources most likely to be read and to influence the target audience. While this flowchart provides details for clinical articles, other flowcharts that integrate the key triggers for a particular reader group (i.e., market researchers, non-clinical researchers) can be readily prepared by one skilled in the art using this flowchart as the basis.

Referring to FIG. 1, at step 100, a literature search is conducted using the relevant search terms. The relevancy of the terms is going to vary depending upon the technology or other subject matter of the search, as is well known. At step 102, duplicate articles or references are purged, by journal category, and at step 104, the title of the first reference is read (as is the abstract, if available).

At step 106 a determination is then made as to whether or not the journal is written in the English language. If not, the process proceeds to step 108, where a determination is made as to whether or not the non-English language journal is directed to a large clinical, epidemiological or post-marketing safety or severe adverse event. If it is determined at step 108 that it is directed to a large clinical, epidemiological or post-marketing safety or sever adverse event, then the process proceeds to step 114 to find out if the article is a journal accessible through a partner library or Internet, or available through an inter-library loan. If it is not available in that manner, it is omitted. However, if at step 114 it is determined that the journal is accessible through a partner library or Internet, then the process proceeds to step 116 where a copy is obtained, and then if necessary, the process proceeds to step 118 where it is translated.

If at step 106 it is determined that the journal is in the English language, the process proceeds to step 110 to determine if it is involved in in vitro or in vivo animal study. If not, the process proceeds to step 114 and is processed as above.

If, however, it is determined that at step 110 that it is an in vitro or in vivo animal study, the process proceeds to step 112 to see if there have been any investigational treatments performed with respect to the in vitro or in vivo animal study. If there have been no investigational treatments performed, then the journal is omitted. If, however, there have been investigational treatments, then the process proceeds to step 114 and proceeds as above.

The above-described process identifies and facilitates the obtaining of the key information resources based upon a reading of titles and abstracts. Once the key information resources have been identified and obtained, the identified resources are ranked objectively to identify the quality of the reference and/or the material contained therein. To do this, in accordance with the present invention, a checklist is used to rank certain elements or pertinence to the field to which the reference is directed. Using a standardized assessment checklist specific to a particular information source type (i.e., for an article, an abstract, or an advertisement, among others), a quantitative percentage score is calculated for each information resource. This score provides a measure of the technical merits of the resource, the presentation of the data in the resource, and deficiencies in the objective aspects of the presentation.

FIG. 2 illustrates an example of one such checklist used to assess the technical merits of an information resource (a clinical article). This is provided only as an example; other checklists which also identify the key aspects of specific information resources (review, books, advertisements) have been developed by Applicant and could developed by one of ordinary skill in the art, given the parameters defined herein. The template of FIG. 2 can be used as a template for the development of additional checklists by one skilled in the art.

Although checklists have been developed to help quantify the process of assessing scientific information, to Applicant's knowledge, none have been developed to the point of a reproducible standard process that can be easily applied to a diverse group of information resources with the goal of providing an objective ranking of the quality of the material. The process described herein addresses shortcoming in inter-rater reliability of previous attempts to assess scientific information.

For example, studies have been performed which compared the results of a simple grading system used by journal peer reviewers and "readers" (clinicians who read the article independently in the journal). These studies found that there was a significant disconnect between the factors that the reviewers thought were important in assessing and article versus what the readers thought. In one study, of the published articles that had been scored highly by the peer-reviewers at the journal, only 33% of the readers thought the manuscript had any relevance to their work. This indicated that even simple survey checklists may not accurately reflect consistently a clinician's perception of the relevancy of a published article.

By contrast, studies performed using the present invention found with strong statistical significance that the rating process and scoring technique of the present invention does consistently reflect a clinician's rating of article relevance to their own clinical practice. This represents a new, validated method to identify key information resources, to survey and score these resources with respect to their information content, and to assess and categorize the content in a consistent manner reflective of an informed reader.

Once the checklist process has been completed to obtain the objective identification of the quality of the reference and/or the material contained therein, the references are subjected to a second process to identify, categorize, and rate key messages contained in those identified information resources (the "Message Identification and Rating Process").

Figure 3A:
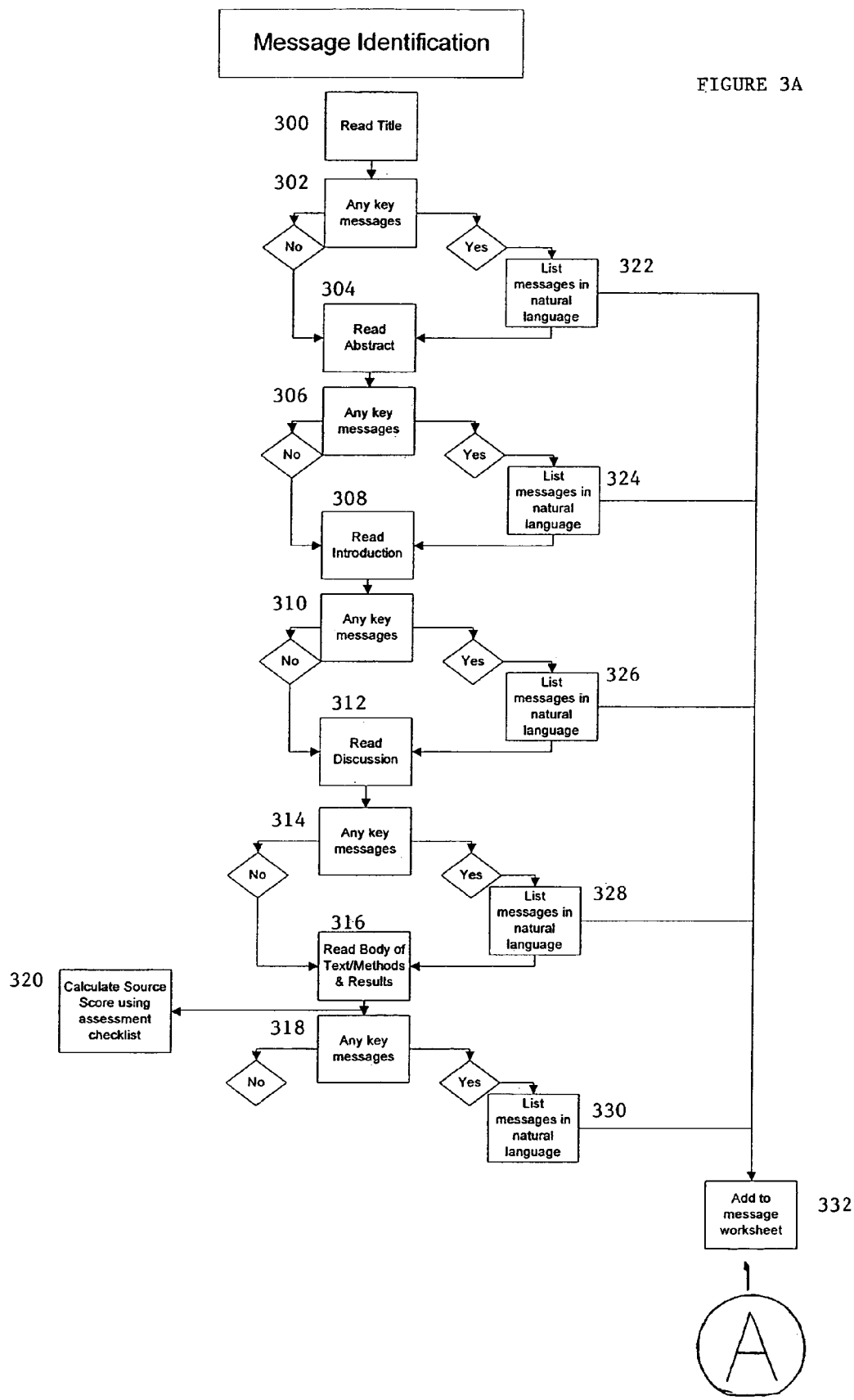
FIGS. 3A and 3B illustrate a flowchart showing the steps performed in connection with the Message Identification and Rating Process of the present invention.
Figure 3B:
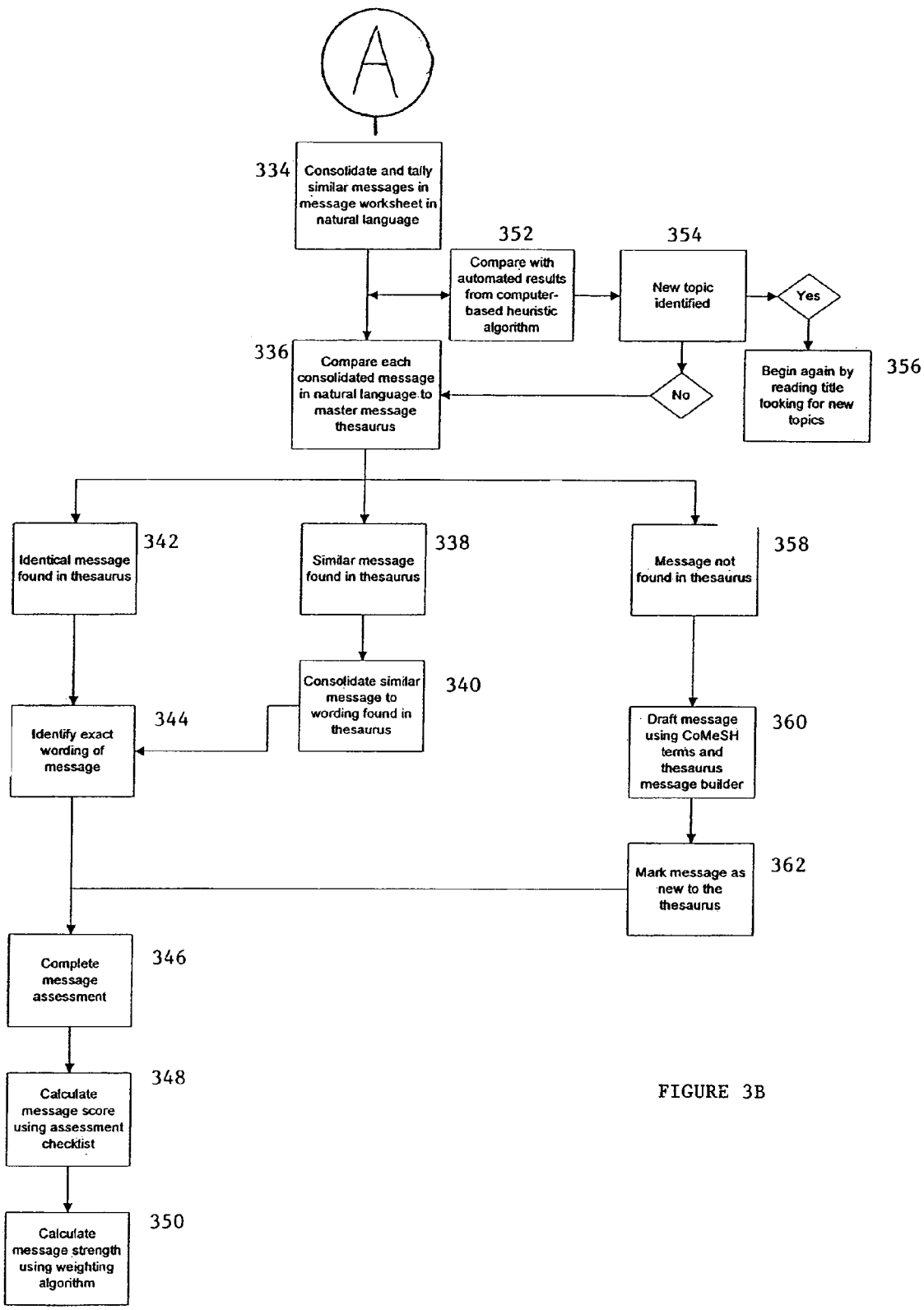

FIGS. 3A and 3B illustrate a flowchart showing the steps performed in connection with the Message Identification and Rating Process. Referring to FIG. 3A, at step 300, the title of the journal article is read, and it is determined if there are any key messages, as identified from the checklist, in the title. If not, the process proceeds to step 304, where the abstract is read. If there are any key messages in the title, then the process proceeds to step 322 which the messages are listed in natural language, and it is added to the message worksheet (step 332) and the process proceeds to step 304 where the abstract is read.

At step 306, a determination is made as to whether or not there are any key messages in the abstract. If not, the process proceeds to step 308 to read introduction. If there are key messages, the messages are listed in natural language (step 324), it is added to the message worksheet (step 332), and then the introduction is read at step 308. At step 310, a determination is made as to whether or not there are any key messages in the introduction. If not, the process proceeds to step 312 where the discussion is read. If there are key messages, the messages are listed in natural language (step 326), it is added to the message worksheet (step 332), and then the discussion is read at step 312.

At step 314, a determination is made as to whether or not there are any key messages in the discussion element of the information resource. If not, the process proceeds to step 316 to read the body of text/method and results. If it is determined that there are key messages, the messages are listed in natural language (step 328), it is added to the message worksheet (step 332), and then the body of text/method and results are read at step 318. At step 320, the source score is calculated using the assessment checklist. If at step 318 it is determined that there are no key messages, the process ends. If there are key messages, the messages are listed in natural language (step 330), it is added to the message worksheet (step 332), and the process ends.

Referring to FIG. 3B, at step 334, similar messages are consolidated and tallied in a message worksheet in the natural language. The process then proceeds to step 336 where each consolidated message is compared in natural language to the master message thesaurus. If there is an identical message found in the thesaurus (step 342), then the process proceeds to step 344 to identify the exact wording of the message, and then a complete message assessment is performed (step 346), and a message score is calculated using the assessment checklist (step 348) from the complete message assessment and then the message strength is calculated using a weighting algorithm at step 350.

If at step 336, a similar message is found in the thesaurus (step 338), then process proceeds to step 340, where similar messages are consolidated with other messages based on wording found in the thesaurus that is similar, and the process then proceeds to step 344 where the process proceeds as above.

If, upon the comparison in step 336, it is determined that the message is not found in the thesaurus (step 358), the process drafts a message using CoMeSH terms and thesaurus message builder updates (step 360), and at step 362, marks the messages as new to the thesaurus. The process then proceeds to step 346 where the process proceeds as above.

Computational algorithms are being developed by independent researchers that potentially have the ability to search for common word strings and patterns within a written document. These programs, if applied to the same resources evaluated by the message identification system described herein, may provide a secondary indication of phrases and concepts repeated within the evaluated resource. This supplemental analysis, though not able to independently identify or interpret a message found in a resource, may provide additional supportive evidence for the existence of a message. The process described herein, therefore, is not dependent upon, but may consider the information derived from such an additional algorithm. This process is illustrated by steps 352, 354, and 356.

A standardized dictionary of message terms (referred to generically in the flowchart of FIG. 3 as the "CoMesh Thesaurus") is developed by the evaluators for each topic. Messages are standardized using the process described in the flowchart of FIG. 3.

For each message so identified in an information resource, a "Message Score" is then calculated. Each message is scored based on whether the message is:
clearly stated,
well supported,
and related to the objective of the information resource.

A Message Score of 0–3 is assigned to each message.

The "Message Strength" is then ultimately calculated for each message. The Message Strength is a numerical representation (out of 100) of the impact the message will have on influencing a reader's attitude toward the topic.

These four factors form the basis of the Message Strength calculation for any message using the present invention, regardless of the application (i.e., medical, non-medical).

| | |
|---|---|
| Quality of information | Astrolytix Source Score |
| Support for key concepts | Message Score |
| Quality of the journal | Journal Impact Factor (JIF)* |
| Format of Presentation | Format score |

The weighting of the individual factors is adjusted periodically to maintain the distribution of message strengths described in previous sections of this application.

The process illustrated in FIGS. 3A and 3B provides a method for consistently identifying, categorizing, and rating key messages contained in those identified information resources. For each message identified in an information resource, a "Message Score" is calculated. The message score is combined with the Source Score and other factors in order to calculate the "Message Strength" for each message. The Message Strength is a numerical representation of the impact the message will have on influencing a reader's attitude toward the topic.

Figure 4:
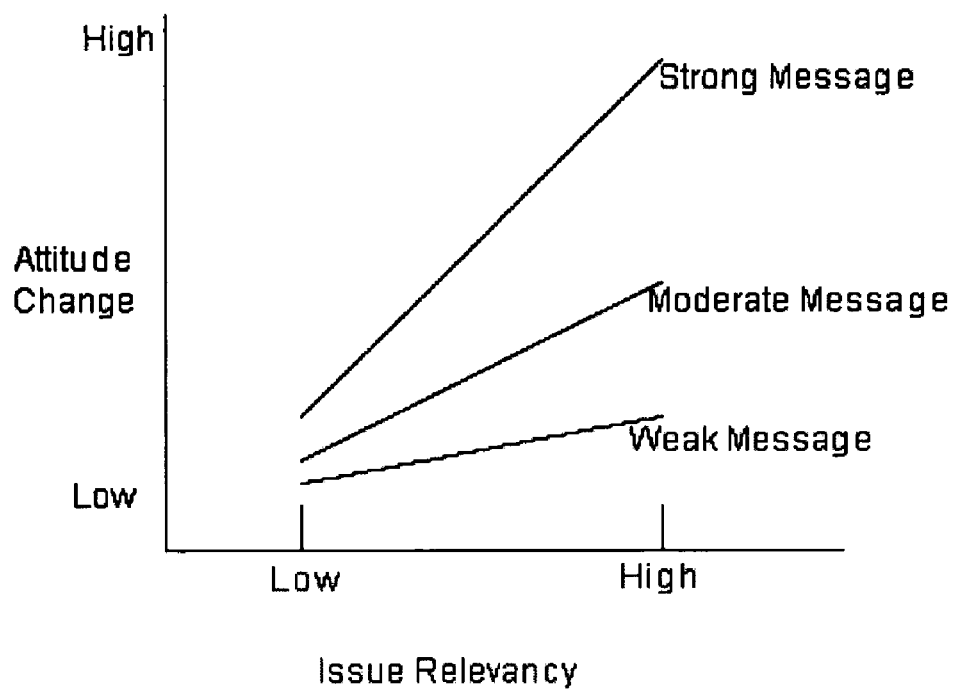
FIG. 4 is a graph illustrating the basis for the need to score resources and rank their identified messages.

Ranking of the strength and quality of messages in an information resource is an important outcome of the process described here. The basis for the need to score resources and rank their identified messages is displayed in the graph of FIG. 4. This statistical analysis indicates that where an issue is of great relevancy to an audience, a message that is presented in a resource convincingly (i.e., with a high Message Strength score) will have a higher probability of influencing a change in the reader's attitude toward that issue.

Using the present invention, a user can consistently determine the key messages promulgated in an information resource, and consistently rate the strength and impact that these messages have on reader opinions.

While the flow process described here is currently implemented by a human evaluator, the process has been designed such that a reader with basic reading skills can implement the system. The message identification flowchart (FIG. 3) allows for the comparison of the results of the human findings to those of an automated, computer-based heuristic algorithm designed to identify key concept patterns; however, this step is not required for the accurate performance of the algorithm.

Using the present invention, the key ideas (messages) described in information resources, including but not limited to books, articles, abstracts, monographs, advertisements, and scientific posters, can be identified, categorized, and quantitatively scored using this process as a proxy, from the point of view of the reader (i.e., consumer, a doctor, researcher, etc).

This process can be used to:
Identify key published information resources in a particular field
Survey and score these information resources with respect to the identity of the key messages and their influence on readers;
Aggregate and categorize message information derived from a set of information resources;
Serve as a proxy for the evaluation process used by readers.

Studies have shown that the most common reported order in which the physicians read the components of their article was:
Title
Abstract
Results or Background
Discussion
Methods The flowchart illustrated in FIGS. 3A and 3B reflects this reading sequence.

The processes of the present invention address selection criteria known to influence reader selection of literature (i.e., study design, journal quality). From a study, seven factors that could influence the impact of an information resource were ranked in the following order of importance by the physicians in the study (n=290).

| Influence | Mean ± SD | Rank |
|---|---|---|
| A. Quality of Information Presented | 4.6 ± 0.68 | 1 |
| B. How Well Key Concepts are Supported by Data | 4.3 ± 0.77 | 2 |
| C. Quality of the Journal | 4.2 ± 0.82 | 3 |
| D. Format of Presentation | 3.8 ± 0.91 | 4 |
| E. Reputation of Sponsor | 3.6 ± 1.02 | 5 |
| F. Reputation of Investigators | 3.6 ± 1.02 | 6 |
| G. Commercial Sponsorship | 2.7 ± 1.01 | 7 |

All comparisons significantly different ($p \leq 0.01$) except for E vs. F ($p = 0.4058$).

The four highlighted factors identified above form the basis of the Message Strength calculation using the present invention, regardless of the application (i.e., medical, non-medical).

| | |
|---|---|
| Quality of information | Source Score |
| Support for key concepts | Message Score |
| Quality of the journal | Journal Impact Factor (JIF)* |
| Format of Presentation | Format score |

*JIF, © Institute for Scientific Information, Philadelphia, PA.

This process of the present invention represents a unique method to identify the subset of information most likely to be read by a target audience, and presents a method to assess the content of information resources and its likely impact on attitudes about that content. Although the examples provided in this application focus on the use of the inventive technique in the scientific arena, this method is broadly applicable to other information-intensive applications, including but not limited to non-pharmaceutical research, assessment of marketing programs, professional and consumer market research, and political campaign analysis, among others.

It is contemplated that some or all of the above-described steps may be implementable using standard well-known programming techniques. The novelty of any such software implementation lies not in the specific programming techniques but in the use of the steps described to achieve the described results. Software programming code which embodies the present invention is typically stored in permanent storage of some type. In a client/server environment, such software programming code may be stored with storage associated with a server. The software programming code may be embodied on any of a variety of known media for use with a data processing system, such as a diskette, or hard drive, or CD ROM. The code may be distributed on such media, or may be distributed to users from the memory or storage of one computer system over a network of some type to other computer systems for use by users of such other systems. The techniques and methods for embodying software program code on physical media and/or distributing software code via networks are well known and will not be further discussed herein.

What is claimed is:

1. A method for identifying a subset of information sources of greatest interest to a target audience from a set of information sources, at least some of which are non-electronic information sources, comprising the steps of:

identifying a quality value of each information source in said set;

identifying the overall key message described in each information source in said set;

categorizing each information source in said set based on its identified key message;

quantitatively scoring each information source in said set based on the interests of said target audience; and identifying the subset of said information sources of greatest interest to said target audience based on said quantitative scoring.

2. The method of claim 1, wherein said identifying of the overall key message is performed by:

separately analyzing logical sections of each information source to identify key messages found in each logical section; and tallying the results of said separate analysis to identify the overall key message of each information source.

3. The method of claim 2 wherein information sources within said set of information sources include at least one of books, articles, abstracts, monographs, advertisements, and scientific posters.

* * * * *